(12) United States Patent
Tofte

(10) Patent No.: US 12,257,172 B2
(45) Date of Patent: Mar. 25, 2025

(54) SENSOR PATCH FOR ATTACHMENT TO A BASE PLATE

(71) Applicant: Coloplast A/S, Humlebaek (DK)

(72) Inventor: Kaare Tofte, Copenhagen S (DK)

(73) Assignee: Coloplast A/S, Humlebaek (DK)

( * ) Notice: Subject to any disclaimer, the term of this patent is extended or adjusted under 35 U.S.C. 154(b) by 566 days.

(21) Appl. No.: 17/434,416

(22) PCT Filed: Feb. 28, 2020

(86) PCT No.: PCT/DK2020/050055
§ 371 (c)(1),
(2) Date: Aug. 27, 2021

(87) PCT Pub. No.: WO2020/173534
PCT Pub. Date: Sep. 3, 2020

(65) Prior Publication Data
US 2022/0142807 A1    May 12, 2022

(30) Foreign Application Priority Data

Feb. 28, 2019  (DK) .......................... PA 2019 70137

(51) Int. Cl.
*A61F 5/44* (2006.01)
*A61F 5/443* (2006.01)

(52) U.S. Cl.
CPC ............ *A61F 5/4404* (2013.01); *A61F 5/443* (2013.01)

(58) Field of Classification Search
CPC ........ A61F 5/4404; A61F 5/443; A61F 5/445; A61F 5/448; A61F 13/0008; A61F 13/0259–0266
See application file for complete search history.

(56) References Cited

U.S. PATENT DOCUMENTS

| | | |
|---|---|---|
| 2,327,514 A | 8/1943 | Fenwick |
| 2,542,233 A | 2/1951 | Carroll |
| 2,544,579 A | 3/1951 | Ardner |
| 3,214,502 A | 10/1965 | Schaar |
| 3,808,354 A | 4/1974 | Feezor et al. |
| 3,832,510 A | 8/1974 | Pfau et al. |
| 3,915,171 A | 10/1975 | Shermeta |
| 3,941,133 A | 3/1976 | Chen |

(Continued)

FOREIGN PATENT DOCUMENTS

| | | |
|---|---|---|
| AU | 2007342523 B2 | 7/2011 |
| CA | 2540756 C | 1/2008 |

(Continued)

*Primary Examiner* — Susan S Su
*Assistant Examiner* — Erin A Kim
(74) *Attorney, Agent, or Firm* — Coloplast Corp., Coloplast A/S; Nick Baumann

(57) ABSTRACT

A sensor patch for attachment to a base plate for an ostomy appliance, the sensor patch having a distal side and an adhesive proximal side, the distal side being adapted for attachment to an adhesive surface of the base plate, wherein the adhesive surface of the base plate is adapted for attachment of the base plate to the skin surface of a user. The sensor patch is provided with a first (100) and a second (150) release liner that are arranged in a way that is nudging the user to release the first release liner first and thereby secure correct application of the sensor patch to the base plate.

13 Claims, 3 Drawing Sheets

(56) References Cited

U.S. PATENT DOCUMENTS

| | | | |
|---|---|---|---|
| 4,231,369 | A | 11/1980 | Sorensen et al. |
| 4,372,308 | A | 2/1983 | Steer et al. |
| 4,449,970 | A | 5/1984 | Bevan et al. |
| 4,668,227 | A | 5/1987 | Kay |
| 4,754,264 | A | 6/1988 | Okada et al. |
| 4,775,374 | A | 10/1988 | Cilento et al. |
| 4,834,731 | A | 5/1989 | Nowak et al. |
| 4,973,323 | A | 11/1990 | Kaczmarek et al. |
| 4,982,742 | A | 1/1991 | Claude |
| 5,013,307 | A | 5/1991 | Broida |
| 5,016,645 | A | 5/1991 | Williams et al. |
| 5,051,259 | A | 9/1991 | Olsen et al. |
| 5,074,851 | A | 12/1991 | Plass et al. |
| 5,111,812 | A | 5/1992 | Swanson et al. |
| 5,147,343 | A | 9/1992 | Kellenberger |
| 5,237,995 | A | 8/1993 | Cano |
| 5,318,543 | A | 6/1994 | Ross et al. |
| 5,322,797 | A | 6/1994 | Mallow et al. |
| 5,358,488 | A | 10/1994 | Suriyapa |
| 5,486,158 | A | 1/1996 | Samuelsen |
| 5,519,644 | A | 5/1996 | Benton |
| 5,570,082 | A | 10/1996 | Mahgerefteh et al. |
| 5,593,397 | A | 1/1997 | La Gro |
| 5,626,135 | A | 5/1997 | Sanfilippo |
| 5,672,163 | A | 9/1997 | Ferreira et al. |
| 5,677,221 | A | 10/1997 | Tseng |
| 5,704,905 | A | 1/1998 | Jensen et al. |
| 5,714,225 | A | 2/1998 | Hansen et al. |
| 5,790,036 | A | 8/1998 | Fisher et al. |
| 5,800,415 | A | 9/1998 | Olsen |
| 5,816,252 | A | 10/1998 | Faries et al. |
| 5,834,009 | A | 11/1998 | Sawers et al. |
| 5,846,558 | A | 12/1998 | Nielsen et al. |
| 5,876,855 | A | 3/1999 | Wong et al. |
| 5,879,292 | A | 3/1999 | Sternberg et al. |
| 5,942,186 | A | 8/1999 | Sanada et al. |
| 6,015,399 | A | 1/2000 | Mracna et al. |
| 6,025,725 | A | 2/2000 | Gershenfeld et al. |
| 6,078,261 | A | 6/2000 | Davsko |
| 6,093,276 | A | 7/2000 | Leise, Jr. et al. |
| 6,101,867 | A | 8/2000 | Cavestri |
| 6,103,033 | A | 8/2000 | Say et al. |
| 6,135,986 | A | 10/2000 | Leisner et al. |
| 6,171,289 | B1 | 1/2001 | Millot et al. |
| 6,206,864 | B1 | 3/2001 | Kavanagh et al. |
| 6,241,704 | B1 | 6/2001 | Peterson et al. |
| 6,246,330 | B1 | 6/2001 | Nielsen |
| 6,270,445 | B1 | 8/2001 | Dean, Jr. et al. |
| 6,407,308 | B1 | 6/2002 | Roe et al. |
| 6,433,244 | B1 | 8/2002 | Roe et al. |
| 6,433,695 | B1 | 8/2002 | Kai et al. |
| 6,482,491 | B1 | 11/2002 | Samuelsen et al. |
| 6,485,476 | B1 | 11/2002 | Von et al. |
| 6,520,943 | B1 | 2/2003 | Wagner |
| 6,677,859 | B1 | 1/2004 | Bensen |
| 6,764,474 | B2 | 7/2004 | Nielsen et al. |
| 6,774,800 | B2 | 8/2004 | Friedman et al. |
| 7,014,816 | B2 | 3/2006 | Miller et al. |
| 7,066,919 | B1 | 6/2006 | Sauerland et al. |
| 7,150,728 | B2 | 12/2006 | Hansen et al. |
| 7,166,091 | B1 | 1/2007 | Zeltner |
| 7,199,501 | B2 | 4/2007 | Pei et al. |
| 7,214,217 | B2 | 5/2007 | Pedersen et al. |
| 7,221,279 | B2 | 5/2007 | Nielsen |
| 7,326,190 | B2 | 2/2008 | Botten |
| 7,341,578 | B2 | 3/2008 | Bulow et al. |
| 7,347,844 | B2 | 3/2008 | Cline et al. |
| 7,367,965 | B2 | 5/2008 | Poulsen et al. |
| 7,422,578 | B2 | 9/2008 | Shan et al. |
| 7,559,922 | B2 | 7/2009 | Botten |
| 7,625,362 | B2 | 12/2009 | Boehringer et al. |
| 7,641,612 | B1 | 1/2010 | McCall |
| 7,670,289 | B1 | 3/2010 | McCall |
| 7,943,812 | B2 | 5/2011 | Stroebeck et al. |
| 7,981,098 | B2 | 7/2011 | Boehringer et al. |
| 8,061,360 | B2 | 11/2011 | Locke et al. |
| 8,277,427 | B2 | 10/2012 | Edvardsen et al. |
| 8,319,003 | B2 | 11/2012 | Olsen et al. |
| 8,326,051 | B1 | 12/2012 | Hobbs |
| 8,343,437 | B2 | 1/2013 | Patel |
| 8,398,575 | B1 | 3/2013 | Mccall |
| 8,398,603 | B2 | 3/2013 | Thirstrup et al. |
| 8,399,732 | B2 | 3/2013 | Oelund et al. |
| 8,409,158 | B2 | 4/2013 | Edvardsen et al. |
| 8,439,883 | B1 * | 5/2013 | Johnsen .................. A61F 5/448 604/338 |
| 8,449,471 | B2 | 5/2013 | Tran |
| 8,474,338 | B2 | 7/2013 | Gelman et al. |
| 8,500,718 | B2 | 8/2013 | Locke et al. |
| 8,507,081 | B2 | 8/2013 | Strobech et al. |
| 8,632,492 | B2 | 1/2014 | Delegge |
| 8,680,991 | B2 | 3/2014 | Tran |
| 8,684,982 | B2 | 4/2014 | Nguyen-Demary et al. |
| 8,707,766 | B2 | 4/2014 | Harris et al. |
| 8,740,865 | B2 | 6/2014 | Krystek et al. |
| 8,795,257 | B2 | 8/2014 | Coulthard et al. |
| 8,821,463 | B2 | 9/2014 | Grum-Schwensen |
| 8,821,464 | B2 | 9/2014 | Hanuka et al. |
| 8,975,465 | B2 | 3/2015 | Hong et al. |
| 8,978,452 | B2 | 3/2015 | Johnson et al. |
| 8,979,813 | B2 | 3/2015 | Uveborn |
| 9,046,085 | B2 | 6/2015 | Schoess et al. |
| 9,066,812 | B2 | 6/2015 | Edvardsen et al. |
| 9,216,104 | B2 | 12/2015 | Thirstrup et al. |
| 9,308,332 | B2 | 4/2016 | Heppe |
| 9,322,797 | B1 | 4/2016 | Lastinger et al. |
| 9,506,886 | B1 | 11/2016 | Woodbury et al. |
| 9,566,383 | B2 | 2/2017 | Yodfat et al. |
| 9,629,779 | B2 | 4/2017 | Grum-Schwensen et al. |
| 9,629,964 | B2 | 4/2017 | Wuepper |
| 9,649,230 | B1 | 5/2017 | Li |
| 9,675,267 | B2 | 6/2017 | Laakkonen et al. |
| 9,693,908 | B2 | 7/2017 | Eriksson et al. |
| 9,770,359 | B2 | 9/2017 | Edvardsen et al. |
| 9,788,991 | B2 | 10/2017 | Bird |
| 9,867,934 | B2 | 1/2018 | Heppe |
| 9,928,341 | B2 | 3/2018 | Angelides |
| 10,016,298 | B2 | 7/2018 | Thirstrup et al. |
| 10,022,277 | B2 | 7/2018 | Heil et al. |
| D826,740 | S | 8/2018 | Stevens et al. |
| 10,426,342 | B2 | 10/2019 | Hresko et al. |
| 10,500,084 | B2 | 12/2019 | Hansen et al. |
| 10,531,977 | B2 | 1/2020 | Schoess et al. |
| 10,646,370 | B2 | 5/2020 | Keleny et al. |
| 10,792,184 | B2 | 10/2020 | Hvid et al. |
| 10,799,385 | B2 | 10/2020 | Hansen et al. |
| 10,849,781 | B2 | 12/2020 | Hansen et al. |
| 10,874,541 | B2 | 12/2020 | Seres et al. |
| 10,987,243 | B2 | 4/2021 | Thirstrup et al. |
| 11,096,818 | B2 | 8/2021 | Thirstrup et al. |
| 11,135,084 | B2 | 10/2021 | Seres et al. |
| 11,219,436 | B2 | 1/2022 | Mayberg |
| 11,238,133 | B1 | 2/2022 | Brewer et al. |
| 11,306,224 | B2 | 4/2022 | Chatterjee et al. |
| 11,406,525 | B2 | 8/2022 | Seres et al. |
| 11,471,318 | B2 | 10/2022 | Hansen et al. |
| 11,612,512 | B2 | 3/2023 | Hansen et al. |
| 11,903,728 | B2 | 2/2024 | Svanegaard et al. |
| 12,064,369 | B2 | 8/2024 | Hansen et al. |
| 2001/0041920 | A1 | 11/2001 | Starkweather et al. |
| 2001/0051787 | A1 | 12/2001 | Haller et al. |
| 2002/0013613 | A1 | 1/2002 | Haller et al. |
| 2002/0019615 | A1 | 2/2002 | Roe et al. |
| 2002/0109621 | A1 | 8/2002 | Khair et al. |
| 2003/0132763 | A1 | 7/2003 | Ellenz |
| 2003/0169032 | A1 | 9/2003 | Minchole et al. |
| 2004/0006320 | A1 | 1/2004 | Buglino et al. |
| 2004/0030305 | A1 | 2/2004 | Sakamoto |
| 2004/0036484 | A1 | 2/2004 | Tamai |
| 2004/0049145 | A1 | 3/2004 | Flick |
| 2004/0078219 | A1 | 4/2004 | Kaylor et al. |
| 2004/0100376 | A1 | 5/2004 | Lye et al. |
| 2004/0106908 | A1 | 6/2004 | Leise et al. |
| 2004/0133175 | A1 | 7/2004 | Hagedorn-Olsen |

(56) References Cited

U.S. PATENT DOCUMENTS

| | | |
|---|---|---|
| 2004/0171999 A1 | 9/2004 | Andersen et al. |
| 2004/0193122 A1 | 9/2004 | Cline et al. |
| 2004/0193123 A1 | 9/2004 | Fenton |
| 2004/0216833 A1 | 11/2004 | Fleming et al. |
| 2005/0038325 A1 | 2/2005 | Moll |
| 2005/0054997 A1 | 3/2005 | Buglino et al. |
| 2005/0065488 A1 | 3/2005 | Elliott |
| 2005/0070863 A1 | 3/2005 | Bulow et al. |
| 2005/0085779 A1 | 4/2005 | Poulsen et al. |
| 2005/0101841 A9 | 5/2005 | Kaylor et al. |
| 2005/0240163 A1 | 10/2005 | Andersen |
| 2005/0256545 A1 | 11/2005 | Koh et al. |
| 2005/0261645 A1 | 11/2005 | Conrad et al. |
| 2006/0015081 A1 | 1/2006 | Suzuki et al. |
| 2006/0025727 A1 | 2/2006 | Boehringer et al. |
| 2006/0052752 A1 | 3/2006 | Mcmichael |
| 2006/0194324 A1 | 8/2006 | Faries et al. |
| 2006/0271002 A1 | 11/2006 | Botten |
| 2007/0035405 A1 | 2/2007 | Wada et al. |
| 2007/0135782 A1 | 6/2007 | Bager et al. |
| 2007/0185464 A1 | 8/2007 | Fattman et al. |
| 2007/0203407 A1 | 8/2007 | Hoss et al. |
| 2007/0204691 A1 | 9/2007 | Bogner et al. |
| 2008/0004580 A1 | 1/2008 | Mullejans et al. |
| 2008/0038536 A1 | 2/2008 | Strobech et al. |
| 2008/0041792 A1 | 2/2008 | Crnkovich et al. |
| 2008/0058740 A1 | 3/2008 | Sullivan et al. |
| 2008/0061965 A1 | 3/2008 | Kuhns et al. |
| 2008/0071214 A1 | 3/2008 | Locke et al. |
| 2008/0075934 A1 | 3/2008 | Barlow et al. |
| 2008/0091154 A1 | 4/2008 | Botten |
| 2008/0140057 A1 | 6/2008 | Wood et al. |
| 2008/0234641 A1 | 9/2008 | Locke et al. |
| 2008/0255808 A1 | 10/2008 | Hayter |
| 2008/0275327 A1 | 11/2008 | Faarbaek et al. |
| 2008/0278337 A1 | 11/2008 | Huang et al. |
| 2008/0300559 A1 | 12/2008 | Gustafson et al. |
| 2008/0300578 A1 | 12/2008 | Freedman |
| 2008/0306459 A1 | 12/2008 | Albrectsen |
| 2009/0012501 A1 | 1/2009 | Boehringer et al. |
| 2009/0118687 A1 | 5/2009 | Kristensen et al. |
| 2009/0167286 A1 | 7/2009 | Naylor et al. |
| 2009/0173935 A1 | 7/2009 | Cho et al. |
| 2009/0216169 A1* | 8/2009 | Hansen ............... A61F 13/0213 206/440 |
| 2009/0227969 A1 | 9/2009 | Jaeb et al. |
| 2009/0234916 A1 | 9/2009 | Cosentino et al. |
| 2009/0247970 A1 | 10/2009 | Keleny et al. |
| 2009/0264957 A1 | 10/2009 | Giftakis et al. |
| 2010/0010460 A1 | 1/2010 | Butler |
| 2010/0030167 A1 | 2/2010 | Thirstrup et al. |
| 2010/0072271 A1 | 3/2010 | Thorstensson |
| 2010/0106220 A1 | 4/2010 | Ecker et al. |
| 2010/0114047 A1 | 5/2010 | Song et al. |
| 2010/0191201 A1 | 7/2010 | Bach et al. |
| 2010/0271212 A1 | 10/2010 | Page |
| 2010/0311167 A1 | 12/2010 | Wood et al. |
| 2011/0034890 A1 | 2/2011 | Stroebech et al. |
| 2011/0071482 A1 | 3/2011 | Selevan |
| 2011/0077497 A1 | 3/2011 | Oster et al. |
| 2011/0130642 A1 | 6/2011 | Jaeb et al. |
| 2011/0144470 A1 | 6/2011 | Mazar et al. |
| 2011/0191044 A1 | 8/2011 | Stafford |
| 2011/0245682 A1 | 10/2011 | Robinson et al. |
| 2011/0246983 A1 | 10/2011 | Brunet et al. |
| 2011/0257496 A1 | 10/2011 | Terashima et al. |
| 2012/0013130 A1 | 1/2012 | Jung |
| 2012/0089037 A1 | 4/2012 | Bishay et al. |
| 2012/0143154 A1 | 6/2012 | Edvardsen et al. |
| 2012/0143155 A1 | 6/2012 | Edvardsen et al. |
| 2012/0258302 A1 | 10/2012 | Hunt et al. |
| 2012/0283678 A1 | 11/2012 | Nguyen-Demary et al. |
| 2012/0304767 A1 | 12/2012 | Howard et al. |
| 2012/0323086 A1 | 12/2012 | Hansen |
| 2013/0018231 A1 | 1/2013 | Hong et al. |
| 2013/0030167 A1 | 1/2013 | Wang et al. |
| 2013/0030397 A1 | 1/2013 | Sabeti |
| 2013/0060213 A1 | 3/2013 | Hanuka et al. |
| 2013/0066285 A1 | 3/2013 | Locke et al. |
| 2013/0072886 A1 | 3/2013 | Schertiger et al. |
| 2013/0078912 A1 | 3/2013 | San Vicente et al. |
| 2013/0086217 A1 | 4/2013 | Price et al. |
| 2013/0102979 A1 | 4/2013 | Coulthard et al. |
| 2013/0138065 A1 | 5/2013 | Buus |
| 2013/0150769 A1 | 6/2013 | Heppe |
| 2013/0165862 A1 | 6/2013 | Griffith et al. |
| 2013/0192604 A1 | 8/2013 | Persson et al. |
| 2013/0226116 A1 | 8/2013 | Edvardsen et al. |
| 2013/0231620 A1 | 9/2013 | Thirstrup et al. |
| 2013/0254141 A1 | 9/2013 | Barda et al. |
| 2013/0303867 A1 | 11/2013 | Elfstrom et al. |
| 2013/0307570 A1 | 11/2013 | Bosaeus et al. |
| 2013/0324952 A1 | 12/2013 | Krystek et al. |
| 2013/0324955 A1 | 12/2013 | Wong et al. |
| 2013/0332085 A1 | 12/2013 | Yang et al. |
| 2014/0051946 A1 | 2/2014 | Arne et al. |
| 2014/0128815 A1 | 5/2014 | Cabiri et al. |
| 2014/0200426 A1 | 7/2014 | Taub et al. |
| 2014/0200538 A1 | 7/2014 | Euliano et al. |
| 2014/0236111 A1 | 8/2014 | Casado et al. |
| 2014/0275854 A1 | 9/2014 | Venkatraman et al. |
| 2014/0276501 A1 | 9/2014 | Cisko |
| 2014/0288381 A1 | 9/2014 | Faarbaek et al. |
| 2014/0303574 A1 | 10/2014 | Knutson |
| 2014/0309600 A1 | 10/2014 | Aceto et al. |
| 2014/0323909 A1 | 10/2014 | Kim |
| 2014/0327433 A1 | 11/2014 | Anway et al. |
| 2014/0336493 A1 | 11/2014 | Kulach et al. |
| 2015/0057634 A1 | 2/2015 | Mastrototaro et al. |
| 2015/0150457 A1 | 6/2015 | Wu et al. |
| 2015/0151051 A1 | 6/2015 | Tsoukalis |
| 2015/0230706 A1 | 8/2015 | Nakagawa et al. |
| 2015/0231802 A1 | 8/2015 | Quan et al. |
| 2015/0250639 A1 | 9/2015 | Thirstrup et al. |
| 2015/0257923 A1 | 9/2015 | Thirstrup et al. |
| 2015/0272495 A1 | 10/2015 | Greener |
| 2015/0328389 A1 | 11/2015 | Heppe |
| 2015/0342777 A1 | 12/2015 | Seres et al. |
| 2015/0374896 A1 | 12/2015 | Du et al. |
| 2016/0008182 A1 | 1/2016 | Prokopuk et al. |
| 2016/0058604 A1 | 3/2016 | Wiltshire et al. |
| 2016/0084869 A1 | 3/2016 | Yuen et al. |
| 2016/0103966 A1 | 4/2016 | Mirza |
| 2016/0117062 A1 | 4/2016 | Hussam et al. |
| 2016/0158056 A1 | 6/2016 | Davis et al. |
| 2016/0158517 A1 | 6/2016 | Nebbia |
| 2016/0158969 A1 | 6/2016 | Mclane et al. |
| 2016/0166438 A1 | 6/2016 | Rovaniemi |
| 2016/0178387 A1 | 6/2016 | Yamasaki et al. |
| 2016/0198996 A1 | 7/2016 | Dullen |
| 2016/0218555 A1 | 7/2016 | Slaby et al. |
| 2016/0235581 A1 | 8/2016 | Keleny et al. |
| 2016/0235582 A1* | 8/2016 | Moavenian ............ A61F 5/448 |
| 2016/0242654 A1 | 8/2016 | Quinlan et al. |
| 2016/0267769 A1 | 9/2016 | Rokhsaz et al. |
| 2016/0278990 A1 | 9/2016 | Chen |
| 2016/0305776 A1 | 10/2016 | Mrtensson et al. |
| 2016/0310077 A1 | 10/2016 | Hunter et al. |
| 2016/0310140 A1 | 10/2016 | Belson et al. |
| 2016/0310329 A1 | 10/2016 | Patel et al. |
| 2016/0331232 A1 | 11/2016 | Love et al. |
| 2016/0331235 A1 | 11/2016 | Nyberg et al. |
| 2016/0361015 A1 | 12/2016 | Wang et al. |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0090236 A1 | 3/2017 | Yeh et al. |
| 2017/0098044 A1 | 4/2017 | Lai et al. |
| 2017/0113001 A1 | 4/2017 | Trock |
| 2017/0140103 A1 | 5/2017 | Angelides |
| 2017/0156920 A1 | 6/2017 | Hunt et al. |
| 2017/0181628 A1 | 6/2017 | Burnette et al. |
| 2017/0340474 A1 | 11/2017 | Thirstrup et al. |
| 2017/0340498 A1 | 11/2017 | Tessmer et al. |

(56) References Cited

U.S. PATENT DOCUMENTS

| | | |
|---|---|---|
| 2017/0348137 A1 | 12/2017 | Hvid et al. |
| 2017/0348162 A1 | 12/2017 | Arizti et al. |
| 2017/0360592 A1 | 12/2017 | Carrubba |
| 2017/0360593 A1 | 12/2017 | Cox |
| 2018/0049667 A1 | 2/2018 | Heppe |
| 2018/0055359 A1 | 3/2018 | Shamim et al. |
| 2018/0110078 A1 | 4/2018 | Mandapaka et al. |
| 2018/0136712 A1 | 5/2018 | Niikura et al. |
| 2018/0171183 A1 | 6/2018 | Sakurai et al. |
| 2018/0177626 A1* | 6/2018 | Israelson ............... A61B 50/30 |
| 2018/0250156 A1 | 9/2018 | Lam |
| 2018/0298240 A1 | 10/2018 | Chatterjee et al. |
| 2018/0318475 A1 | 11/2018 | Thomson et al. |
| 2018/0344533 A1 | 12/2018 | Rovaniemi |
| 2019/0008439 A1 | 1/2019 | Sageder et al. |
| 2019/0133810 A1 | 5/2019 | Seres et al. |
| 2019/0133811 A1 | 5/2019 | Seres et al. |
| 2019/0133812 A1 | 5/2019 | Seres et al. |
| 2019/0142623 A1 | 5/2019 | Schoess et al. |
| 2019/0175386 A1 | 6/2019 | Monty |
| 2019/0184093 A1 | 6/2019 | Sjolund et al. |
| 2019/0192066 A1 | 6/2019 | Schoess et al. |
| 2019/0192332 A1 | 6/2019 | Hansen et al. |
| 2019/0192333 A1 | 6/2019 | Hansen et al. |
| 2019/0192334 A1 | 6/2019 | Hansen et al. |
| 2019/0240059 A1 | 8/2019 | Seres et al. |
| 2019/0247050 A1 | 8/2019 | Goldsmith |
| 2019/0252079 A1 | 8/2019 | Constantin et al. |
| 2019/0374163 A1 | 12/2019 | Faarbaek et al. |
| 2020/0000624 A1 | 1/2020 | Gibbons et al. |
| 2020/0078206 A1 | 3/2020 | Chiladakis |
| 2020/0100931 A1 | 4/2020 | Schoess et al. |
| 2020/0114535 A1 | 4/2020 | Wattam et al. |
| 2020/0188161 A1 | 6/2020 | Seres et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0276063 A1 | 9/2020 | Muñoz Herencia |
| 2020/0279368 A1 | 9/2020 | Tada et al. |
| 2020/0297244 A1 | 9/2020 | Brownhill et al. |
| 2020/0306074 A1 | 10/2020 | Speiermann et al. |
| 2020/0322793 A1 | 10/2020 | Yang |
| 2020/0330258 A1 | 10/2020 | Hansen et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0375499 A1 | 12/2020 | Hansen et al. |
| 2020/0375782 A1 | 12/2020 | Hansen et al. |
| 2020/0375783 A1 | 12/2020 | Hansen et al. |
| 2020/0375784 A1 | 12/2020 | Hansen et al. |
| 2020/0375785 A1 | 12/2020 | Hansen et al. |
| 2020/0375786 A1 | 12/2020 | Hansen et al. |
| 2020/0375809 A1 | 12/2020 | Sullivan et al. |
| 2020/0383637 A1 | 12/2020 | Hansen et al. |
| 2020/0383818 A1 | 12/2020 | Hansen et al. |
| 2020/0383819 A1 | 12/2020 | Sletten et al. |
| 2020/0383820 A1 | 12/2020 | Hansen et al. |
| 2020/0383821 A1 | 12/2020 | Hansen et al. |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1 | 1/2021 | Hansen et al. |
| 2021/0000634 A1 | 1/2021 | Svanegaard et al. |
| 2021/0000635 A1 | 1/2021 | Hansen et al. |
| 2021/0000636 A1 | 1/2021 | Hansen et al. |
| 2021/0007663 A1 | 1/2021 | Svanegaard et al. |
| 2021/0007881 A1 | 1/2021 | Svanegaard et al. |
| 2021/0015653 A1 | 1/2021 | Hansen et al. |
| 2021/0015654 A1 | 1/2021 | Hansen et al. |
| 2021/0022683 A1 | 1/2021 | Faarbaek et al. |
| 2021/0038424 A1 | 2/2021 | Svanegaard et al. |
| 2021/0059603 A1 | 3/2021 | Svanegaard et al. |
| 2021/0085511 A1 | 3/2021 | Hansen et al. |
| 2021/0085512 A1 | 3/2021 | Hansen et al. |
| 2021/0100533 A1 | 4/2021 | Seres et al. |
| 2021/0128364 A1 | 5/2021 | Cole et al. |
| 2021/0145354 A1 | 5/2021 | Hunt et al. |
| 2021/0177642 A1 | 6/2021 | Andersen et al. |
| 2021/0212855 A1 | 7/2021 | Hansen et al. |
| 2021/0228194 A1 | 7/2021 | Mayberg |
| 2021/0338471 A1 | 11/2021 | Nolan et al. |
| 2021/0361464 A1 | 11/2021 | Larsen et al. |
| 2021/0361465 A1 | 11/2021 | Hansen et al. |
| 2021/0361466 A1 | 11/2021 | Hansen et al. |
| 2021/0361467 A1 | 11/2021 | Hansen et al. |
| 2021/0369197 A1 | 12/2021 | Hansen et al. |
| 2021/0369488 A1 | 12/2021 | Hansen et al. |
| 2021/0369489 A1 | 12/2021 | Hansen et al. |
| 2021/0369490 A1 | 12/2021 | Hansen et al. |
| 2021/0370217 A1 | 12/2021 | Kirschman |
| 2021/0386368 A1 | 12/2021 | Carlsson et al. |
| 2022/0000652 A1 | 1/2022 | Thirstrup et al. |
| 2022/0031227 A1 | 2/2022 | Cho et al. |
| 2022/0031495 A1 | 2/2022 | Seres et al. |
| 2022/0079802 A1 | 3/2022 | Hansen |
| 2022/0079803 A1 | 3/2022 | Windeballe et al. |
| 2022/0087851 A1* | 3/2022 | Stroebech ............ A61B 5/6833 |
| 2022/0110585 A1 | 4/2022 | Andersen |
| 2022/0117771 A1 | 4/2022 | Fearn et al. |
| 2022/0142807 A1 | 5/2022 | Tofte |
| 2022/0192860 A1 | 6/2022 | Hansen et al. |
| 2022/0241104 A1* | 8/2022 | Knoedler ................ A61F 5/443 |
| 2022/0241105 A1 | 8/2022 | Hansen et al. |
| 2022/0265458 A1 | 8/2022 | Carlsson et al. |
| 2022/0304844 A1 | 9/2022 | Carlsson et al. |
| 2023/0059470 A1 | 2/2023 | Hansen et al. |
| 2023/0064734 A1 | 3/2023 | Hansen et al. |
| 2023/0105402 A1 | 4/2023 | Hansen et al. |
| 2023/0117727 A1 | 4/2023 | Hansen et al. |
| 2023/0118594 A1 | 4/2023 | Speiermann et al. |
| 2023/0141297 A1* | 5/2023 | Herold .................... A61F 5/445 |
| | | 604/344 |
| 2023/0141719 A1 | 5/2023 | Emborg et al. |
| 2023/0142141 A1 | 5/2023 | Emborg et al. |
| 2023/0145670 A1 | 5/2023 | Seres et al. |
| 2023/0146436 A1 | 5/2023 | Hansen et al. |
| 2023/0147665 A1 | 5/2023 | Hasbeck et al. |
| 2023/0190509 A1 | 6/2023 | Hansen et al. |
| 2023/0210682 A1 | 7/2023 | Hansen et al. |
| 2023/0233147 A1 | 7/2023 | Hansen et al. |
| 2023/0255811 A1 | 8/2023 | Carlsson et al. |
| 2023/0284932 A1 | 9/2023 | Hansen et al. |
| 2023/0293333 A1 | 9/2023 | Hansen et al. |
| 2023/0293335 A1 | 9/2023 | Hansen et al. |
| 2023/0301818 A1 | 9/2023 | Hansen et al. |
| 2023/0310201 A1 | 10/2023 | Hansen et al. |
| 2023/0329893 A1 | 10/2023 | Olsen et al. |
| 2023/0338005 A1 | 10/2023 | Barthe et al. |
| 2023/0372141 A1 | 11/2023 | Larsen et al. |
| 2023/0414397 A1 | 12/2023 | Hansen et al. |
| 2024/0009020 A1 | 1/2024 | Hansen et al. |
| 2024/0041635 A1 | 2/2024 | Hansen et al. |
| 2024/0180740 A1 | 6/2024 | Hansen et al. |
| 2024/0225539 A1 | 7/2024 | Svanegaard et al. |
| 2024/0261130 A1 | 8/2024 | Hansen et al. |

FOREIGN PATENT DOCUMENTS

| | | |
|---|---|---|
| CA | 3009449 C | 9/2019 |
| CA | 3002372 C | 3/2021 |
| CA | 2947016 C | 2/2023 |
| CN | 103269668 A | 8/2013 |
| CN | 203786580 U | 8/2014 |
| CN | 104902399 A | 9/2015 |
| CN | 104980878 A | 10/2015 |

(56) References Cited

FOREIGN PATENT DOCUMENTS

| | | |
|---|---|---|
| CN | 105588856 A | 5/2016 |
| CN | 106062546 A | 10/2016 |
| CN | 206271160 U | 6/2017 |
| CN | 206450708 U | 8/2017 |
| CN | 105615896 B | 5/2019 |
| CN | 105359167 B | 6/2019 |
| DE | 3437950 A1 | 4/1985 |
| DE | 3836590 A1 | 5/1990 |
| DE | 19953062 A1 | 5/2000 |
| DE | 19900611 C1 | 7/2000 |
| DE | 102011014321 A1 | 9/2012 |
| DE | 102011076219 A1 | 11/2012 |
| EP | 0168967 A1 | 1/1986 |
| EP | 0373782 A1 | 6/1990 |
| EP | 0416397 A1 | 3/1991 |
| EP | 0850076 B1 | 4/2005 |
| EP | 1188157 B1 | 12/2005 |
| EP | 2108345 A1 | 10/2009 |
| EP | 2489561 A2 | 8/2012 |
| EP | 2654646 A2 | 10/2013 |
| EP | 2453851 B1 | 10/2014 |
| EP | 3064179 A1 | 9/2016 |
| EP | 3213727 A1 | 9/2017 |
| GB | 2219679 A | 12/1989 |
| GB | 2225951 A | 6/1990 |
| GB | 2308306 A1 | 6/1997 |
| GB | 2343628 A | 5/2000 |
| GB | 2465742 A | 6/2010 |
| GB | 2542093 A | 3/2017 |
| JP | 04-074882 A | 3/1992 |
| JP | 06-152077 A | 5/1994 |
| JP | 09-010184 A | 1/1997 |
| JP | 11-128352 A | 5/1999 |
| JP | 2000-093448 A | 4/2000 |
| JP | 2001-087299 A | 4/2001 |
| JP | 2002-055074 A | 2/2002 |
| JP | 2002-224093 A | 8/2002 |
| JP | 2005-323981 A | 11/2005 |
| JP | 2007-319561 A | 12/2007 |
| JP | 2014-033745 A | 2/2014 |
| JP | 2014-054368 A | 3/2014 |
| JP | 2014-507182 A | 3/2014 |
| JP | 2014151096 A | 8/2014 |
| KR | 101056989 B1 | 8/2011 |
| KR | 10-2012-0003987 A | 1/2012 |
| KR | 20170003918 U | 11/2017 |
| KR | 200485138 Y1 | 12/2017 |
| NL | 1001019 C2 | 2/1997 |
| NL | 1003904 C2 | 3/1998 |
| RU | 2527155 C2 | 8/2014 |
| TW | 201201783 A | 1/2012 |
| WO | 94/15562 A1 | 7/1994 |
| WO | 97/10012 A1 | 3/1997 |
| WO | 99/33037 A1 | 7/1999 |
| WO | 99/36017 A1 | 7/1999 |
| WO | 00/79497 A1 | 12/2000 |
| WO | 01/13830 A1 | 3/2001 |
| WO | 01/50996 A1 | 7/2001 |
| WO | 02/52302 A2 | 7/2002 |
| WO | 02/99765 A1 | 12/2002 |
| WO | 2004084778 A2 | 10/2004 |
| WO | 2005/038693 A1 | 4/2005 |
| WO | 2005/082271 A2 | 9/2005 |
| WO | 2006/008866 A1 | 1/2006 |
| WO | 2006/094513 A2 | 9/2006 |
| WO | 2007/000168 A1 | 1/2007 |
| WO | 2007/059774 A2 | 5/2007 |
| WO | 2007/070266 A1 | 6/2007 |
| WO | 2007098762 A1 | 9/2007 |
| WO | 2007/133555 A2 | 11/2007 |
| WO | 2007128038 A1 | 11/2007 |
| WO | 2008/057884 A2 | 5/2008 |
| WO | 2009/006900 A1 | 1/2009 |
| WO | 2009/052496 A1 | 4/2009 |
| WO | 2009/107011 A1 | 9/2009 |
| WO | 2009/112912 A2 | 9/2009 |
| WO | 2011/003421 A1 | 1/2011 |
| WO | 2011/004165 A1 | 1/2011 |
| WO | 2011003420 A1 | 1/2011 |
| WO | 2011/061540 A1 | 5/2011 |
| WO | 2011/105701 A2 | 9/2011 |
| WO | 2011/123018 A1 | 10/2011 |
| WO | 2011/139499 A1 | 11/2011 |
| WO | 2011/161254 A2 | 12/2011 |
| WO | 2012/068386 A1 | 5/2012 |
| WO | 2012/076022 A2 | 6/2012 |
| WO | 2012/084987 A2 | 6/2012 |
| WO | 2013/013197 A1 | 1/2013 |
| WO | 2013095231 A1 | 6/2013 |
| WO | 2013164517 A1 | 11/2013 |
| WO | 2014/004207 A1 | 1/2014 |
| WO | 2014/086369 A1 | 6/2014 |
| WO | 2014116816 A1 | 7/2014 |
| WO | 2015/007284 A1 | 1/2015 |
| WO | 2015/014774 A1 | 2/2015 |
| WO | 2015/084462 A1 | 6/2015 |
| WO | 2015/094064 A1 | 6/2015 |
| WO | 2015/187366 A1 | 12/2015 |
| WO | 2015186452 A1 | 12/2015 |
| WO | 2016124202 A1 | 8/2016 |
| WO | 2016132738 A1 | 8/2016 |
| WO | 2016/166731 A1 | 10/2016 |
| WO | 2016162038 A1 | 10/2016 |
| WO | 2016192738 A1 | 12/2016 |
| WO | 2017/023794 A1 | 2/2017 |
| WO | 2017/062042 A1 | 4/2017 |
| WO | 2017/067558 A1 | 4/2017 |
| WO | 2017/067560 A1 | 4/2017 |
| WO | 2017/074505 A1 | 5/2017 |
| WO | 2017/088153 A1 | 6/2017 |
| WO | 2017108109 A1 | 6/2017 |
| WO | 2017/136696 A1 | 8/2017 |
| WO | 2017/190752 A1 | 11/2017 |
| WO | 2018/028756 A1 | 2/2018 |
| WO | 2019/094635 A1 | 5/2019 |
| WO | 2019/120432 A1 | 6/2019 |
| WO | 2019/161859 A1 | 8/2019 |
| WO | 2019/161860 A1 | 8/2019 |
| WO | 2019/161863 A1 | 8/2019 |
| WO | 2019/174693 A1 | 9/2019 |
| WO | 2019/174695 A1 | 9/2019 |
| WO | 2019/213623 A1 | 11/2019 |
| WO | 2020/035121 A1 | 2/2020 |

\* cited by examiner

SENSOR PATCH FOR ATTACHMENT TO A BASE PLATE

The invention relates to a sensor patch for attachment to a base plate for an ostomy appliance and a method of attaching such sensor patch to an ostomy base plate.

BACKGROUND

Stomal output often contains body fluids and visceral contents that are aggressive to both the skin of a user and to ostomy devices, these have a detrimental effect on the efficiency and integrity of the adhesive materials that are applied to attach the ostomy device to the user's skin surface. For users in general safe, reliable and efficient ostomy devices are evidently highly desirable.

However, a particularly major and persistent concern of a large population of ostomists continues to be failure of the base plate adhesive attaching the ostomy appliance to the user's skin surface, because such failure almost inevitably leads to embarrassing and stigmatising leakage incidents. Such incidents in turn are known from several user interviews to lead to a reduced quality-of-life feeling. Adhesive failure of the base plate adhesive can result from various reasons. Most often, a leakage incident is caused by stomal output entering between the proximal surface of the base plate and the user's skin, e.g. due to less-than-optimal attachment of the base plate to the skin arising from e.g. uneven skin surface or skin folds. This undesirable progression of stomal output "underneath" the adhesive leads to deterioration and/or weakening of the adhesive material carrying the weight and providing the seal of the ostomy appliance. Often such failure happens surprisingly fast and is only detectable for the user once the failure has already become so severe that leakage occurs, requiring immediate change of the ostomy appliance and possibly also of the user's clothes.

In other instances, the primary factor of adhesive failure is simply a question of how much time has elapsed since the base plate of the ostomy appliance was first applied to the user's skin surface. In addition to the output from the stoma itself, the peristomal skin surface continuously secretes some moisture (e.g. sweat). To mitigate this, most often adhesives of base plates for ostomy devices include hydrocolloid materials which are capable of absorbing high levels of moisture, thereby stabilizing the polymer matrix of the adhesive material and prolonging the lifetime ("wear time") of the base plate. However, eventually the adhesion capability of the base plate no longer can support the force exerted on the base plate from the load of the output collecting bag, and the appliance must be replaced.

As there can be considerable differences in the severity and/or speed by which adhesive failure and potentially leakage occur, which differences at least to some extent are correlated to various factors including those presented above, a mere indication that failure or leakage is imminent, or that it has already occurred, fails to represent a reliable and satisfactory solution to the problem of avoiding sudden embarrassing and stigmatising leakage incidents in ostomy appliances. In other words, the users of ostomy appliances could greatly benefit from an appliance solution which provides them with better guidance and options regarding how and not least how quickly to react to beginning failure or leakage of the adhesive of the base plate of the appliance. More generally, ostomists and health care professionals alike would welcome improvements in ostomy devices to reduce or eliminate the occurrence of sudden leakage incidents.

SUMMARY OF THE INVENTION

Disclosed is a sensor patch for attachment to a base plate for an ostomy appliance and a method for attaching such sensor patch to a base plate. The sensor patch having a proximal side and a distal side. The distal side being adapted for attachment to an adhesive surface of the base plate, wherein the adhesive surface of the base plate is adapted for attachment of the base plate to the skin surface of a user. The sensor patch is provided with a first release liner and a second release liner that facilitates easy and correct application of the sensor patch to the base plate.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
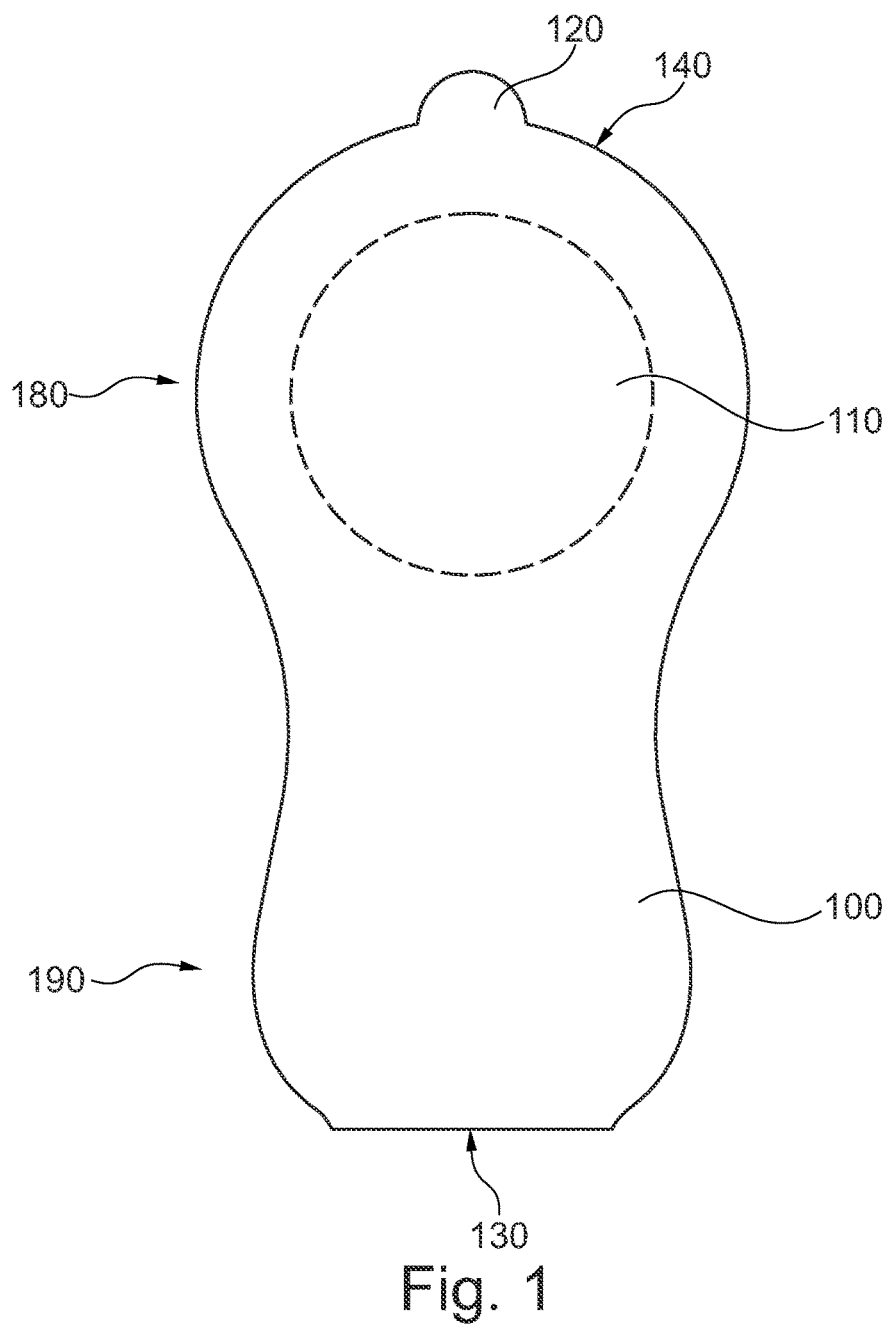
FIG. 1 illustrates an embodiment of a sensor patch seen from the distal side.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with respect to the orientation of the Figure(s) being described. Because components of embodiments can be positioned in a number of different orientations, the directional terminology is used for purposes of illustration and is in no way limiting. It is to be understood that other embodiments may be utilized, and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side the side furthest away from the user in use.

The axial direction is defined as the direction of the stoma, when the appliance is worn by a user. Thus, the axial direction is generally perpendicular to the skin or abdominal surface of the user.

The radial direction is defined as transverse to the axial direction that is transversely to the direction of the stoma, i.e. "across" the distal/proximal surface of the base plate. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The use of the word "essentially" as a qualifier to certain structural and functional features or effects in this disclosure is used for emphasizing what is the most important focus of something or fact about something (i.e. a feature may have or fulfil a variety of effects, but when the disclosure discusses one effect as being "essentially" provided, this is the focus and the most important effect in relation to the disclosure).

Throughout the disclosure, the use of the terms "first", "second", "third", "fourth", "primary", "secondary", "tertiary" etc. does not imply any particular order or importance but are included merely to identify individual elements. Furthermore, the labelling of a first element does not imply the presence of a second element and vice versa.

Disclosed is a sensor patch for attachment to a base plate for an ostomy appliance. Such as to facilitate detection of moisture propagation in the adhesive material provided for attaching the base plate to the skin surface of a user as well as detection of increased risk of leakage. For example, the sensor patch may allow electronic measurements of performance of the base plate and/or to facilitate detection of increasing risks of leakage and/or to facilitate detection of decreasing adherence of the base plate to the skin of the user.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. For example, the base plate may comprise a coupling ring for coupling an ostomy pouch to the base plate. Further, a two-part ostomy appliance may facilitate correct application of the base plate to skin, e.g. to an improved user sight of the stomal region. Alternatively, the ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The base plate may comprise a first adhesive layer, i.e. a first layer of an adhesive material. During use, a proximal surface of the first adhesive layer adheres to the user's skin in the peristomal area and/or to additional seals, such as sealing paste, sealing tape and/or sealing ring. The first adhesive layer may be made of a first composition. The first composition may comprise one or more polyisobutenes and/or styrene-isoprene-styrene. The first composition may comprise one or more hydrocolloids. The first composition may comprise one or more water soluble or water swellable hydrocolloids. The first composition may be a pressure sensitive adhesive composition suitable for medical purposes comprising a rubbery elastomeric base and one or more water soluble or water swellable hydrocolloids. The first adhesive layer may comprise a distal surface and a proximal surface. The proximal surface of the first adhesive layer may be configured to adhere to the user's skin. The distal surface of the first adhesive layer may be configured to face away from the skin of the user.

The first adhesive layer may form the adhesive surface of the base plate adapted for attachment of the base plate to the skin surface of the user. The first adhesive layer may form part of the adhesive surface of the base plate adapted for attachment of the base plate to the skin surface of the user.

The base plate may comprise a second adhesive layer, i.e. a second layer of an adhesive material, also denoted rim adhesive layer. The second adhesive layer may be of a different adhesive material than the first adhesive layer. The second adhesive layer may be made of a second composition. The second composition may comprise one or more polyisobutenes and/or styrene-isoprene-styrene. The second composition may comprise one or more hydrocolloids. The second composition may comprise one or more water soluble or water swellable hydrocolloids. The second composition may be a pressure sensitive adhesive composition suitable for medical purposes comprising a rubbery elastomeric base and one or more water soluble or water swellable hydrocolloids. The second adhesive layer may comprise a distal surface and a proximal surface. The proximal surface of the second adhesive layer may be configured to adhere to the user's skin, e.g. at least at a rim portion of the second adhesive layer. The distal surface of the second adhesive layer may be configured to face away from the skin of the user. The second adhesive layer may be covering a larger area than the first adhesive layer, e.g. such that the proximal surface of the second adhesive layer forms an adhesive rim surrounding the first adhesive layer.

The sensor patch is adapted for attachment to the base plate. For example, the sensor patch may be configured to be positioned between the skin of the user and the proximal side of the base plate. For example, the sensor patch may be adapted for attachment to the first adhesive layer of the base plate. For example, a distal side of the sensor patch may be configured to be facing the proximal surface of the first adhesive layer of the base plate. For example, the sensor patch, such as a distal side of the sensor patch may be configured to adhere to the proximal surface of the first adhesive layer of the base plate.

The sensor patch may comprise a stomal opening and/or the sensor patch may be adapted to form a stomal opening. Each layer of the sensor patch, as described below, may comprise stomal openings and/or be adapted to form a stomal opening for collectively forming the stomal opening of the sensor patch. The stomal opening of the sensor patch may be configured to be aligned with the stomal opening of the base plate, such as to collectively form the stomal opening of the combined base plate and sensor patch. The size and/or shape of the stomal opening of the sensor patch may be adjusted by the user or nurse before application of the sensor patch to accommodate the user's stoma. The size and/or shape of the stomal opening of the sensor patch may be adjusted together with adjustment of the stomal opening of the base plate, e.g. after the sensor patch has been attached to the base plate. The stomal opening(s) may have a centre point.

The sensor patch may comprise a sensor assembly. The sensor assembly may form a sensor assembly layer. The sensor assembly may have a distal side and a proximal side. The sensor patch may be configured to be positioned on the base plate such that the distal surface of the sensor assembly is coupled to the proximal adhesive surface of the base plate.

The sensor assembly may comprise a plurality of electrodes. The plurality of electrodes may include a first electrode and a second electrode for forming a first sensor. The plurality of electrodes may include a third electrode, a fourth electrode, a fifth electrode and/or a sixth electrode. The first electrode may be a common ground electrode. For example, a second sensor may be formed by the first electrode and the third electrode, a third sensor may be formed by the first electrode and the fourth electrode, a fourth electrode may be formed by the first electrode and the fifth electrode, and/or a fifth electrode may be formed by the first electrode and the sixth electrode. Each electrode may have respective connection parts for connecting the electrodes to respective terminal elements of a monitor device.

The plurality of electrodes is electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

The plurality of electrodes may form loops and/or open loops. Open loop electrode(s) enables electrode arrangement in few or a single electrode layer.

The sensor assembly may comprise a support layer, e.g. with a proximal surface and a distal surface. The plurality of electrodes may be provided, such as formed, on the proximal surface of the support layer, e.g. the plurality of electrodes may be positioned on the proximal surface of the support layer.

The sensor assembly may comprise a masking element, e.g. with a proximal surface and a distal surface. The masking element may be configured to electrically insulate at least parts of the plurality of electrodes from proximal layers, such as a first adhesive sensor layer. The masking element may cover or overlap parts of the plurality electrodes, e.g. when seen in the axial direction.

The sensor patch may comprise a first adhesive sensor layer, e.g. with a proximal side and a distal side. The first adhesive sensor layer may be arranged on a proximal side of the sensor assembly. The first adhesive sensor layer, such as the proximal side of the first adhesive sensor layer, may form the proximal side of the sensor patch. The proximal side of the first adhesive sensor layer may be configured to adhere to the user's skin. Thus, after being applied to the base plate, the combined base plate and sensor patch may form an adhesive proximal surface configured to be applied to the skin surface of the user. The first adhesive sensor layer may be made of a first adhesive sensor material, such as the first composition, the second composition or a third composition. The third composition may comprise one or more polyisobutenes and/or styrene-isoprene-styrene. The third composition may comprise one or more hydrocolloids. The third composition may comprise one or more water soluble or water swellable hydrocolloids. The third composition may be a pressure sensitive adhesive composition suitable for medical purposes comprising a rubbery elastomeric base and one or more water soluble or water swellable hydrocolloids.

The sensor patch is adapted to form a stomal opening with a centre point. The stomal opening is configured to allow passage of output through the stomal opening and into an ostomy pouch attached to the base plate.

Arranging the sensor patch correctly on the base plate can be difficult for the user. It is important that the sensor patch is oriented correctly, with the distal side facing the base plate and the proximal side facing the skin of the user. If the sensor is applied wrongly, with the distal side facing the skin, several problems may arise. The sensors will not work properly as they do not contact the skin surface the way they are configured to, and the base plate may not adhere properly to the skin as the distal side of the sensor patch may not comprise the same adhesive properties as the proximal side—or it may even be non-adhesive. This may result in undesired leakage.

As the sensor patch may allow electronic measurements of performance of the base plate and/or to facilitate detection of increasing risks of leakage and/or to facilitate detection of decreasing adherence of the base plate to the skin of the user, it is important that the sensor patch is oriented correctly. Electrodes need to be positioned correctly in order to perform its function and if the sensor patch may be oriented wrongly, then for example the electrodes may be embedded in adhesive instead of being in contact with the skin which evidently will lead to false measurements.

In aspects, a sensor patch where the release liners guide the user to apply the sensor patch correctly to the base plate is provided.

Embodiments relate to a sensor patch for attachment to a base plate for an ostomy appliance, the sensor patch having a distal side and an adhesive proximal side, the distal side being adapted for attachment to an adhesive surface of the base plate, wherein the adhesive surface of the base plate is adapted for attachment of the base plate to the skin surface of a user, the sensor patch comprises a first edge portion and a second edge portion, the second edge portion being positioned substantially opposite the first edge portion, a first release liner covering the distal side of the sensor patch and a second release liner covering the proximal adhesive side of the sensor patch, wherein the first release liner extends over and around the first edge portion to cover a part of the proximal side of the sensor patch to defining an overlapping section where the first release liner partially overlaps the second release liner.

The sensor patch is provided with a first release liner on the distal side and a second release liner on the proximal side. The release liners may protect the sensor patch during storage and before use by covering the adhesive surface and the electronics. In order to secure correct application of the sensor patch to the base plate, the release lines are arranged in a way that nudges the user to remove the first release liner first, thereby exposing the distal surface of the sensor patch first and applying this to the base plate.

Then the second release liner can be removed and the base plate with sensor patch can be applied to the skin of a user. By having an overlapping section where the first release liner lies on top of the second release liner, it will be difficult and non-intuitive for the user to remove the second release liner first and thereby risking wrong orientation of the sensor patch on the base plate. The overlapping section "locks" one end of the second release liner and thereby nudges the user to remove the first release liner first.

In embodiments, the first release liner may be removed by pulling a tab member at a second edge portion of the sensor patch or it may be removed by loosening the first release liner at the overlapping section and pulling it off.

In embodiments, the first release liner overlies the second release liner at the overlapping section so the portion of the second release liner being under/overlapped by the first release liner cannot be accessed without removing the overlapping section of the first release liner.

In embodiments, the first release liner is releasably attached to the second release liner at the overlapping section. The first release liner may be attached to the second release liner by for example adhesive or lamination/welding. In embodiments, the first release liner and the second release liner are inseparately connected at the overlapping section. This allows the user to use the first release liner as handle/tab member while releasing the second release liner. In embodiments, the first release liner and the second release liner are connected at the first edge portion of the sensor patch to define a continuous sheet. In embodiments, the first release liner and the second release liner are made from a single sheet of material, being folded around the first edge portion of the sensor patch.

In embodiments, the distal side of the sensor patch is non-adhesive. In embodiments, the sensor patch may be provided with a top film on the distal side. As the sensor patch is adhered to the base plate by the adhesive surface of the base plate, no adhesive is needed. Furthermore, in the case that the sensor patch is extending further than the base plate, a non-adhesive distal side may be advantageous in order not to stick to the clothes of the user.

In embodiments, the first release liner is provided with an adhesive side, the adhesive side being the surface facing the distal side of the sensor patch. Hence the first release liner can adhere to a non-adhesive surface of the sensor patch. In embodiments, the second release liner is non-adhesive and can be releasably attached to the proximal adhesive surface of the sensor patch. In embodiments, the second release liner is provided with a non-stick surface (siliconized) facing the sensor patch.

In embodiments, the sensor patch comprises a central section and a peripheral section. In embodiments, the central section is provided with a stomal opening. When the sensor patch is applied to a base plate, the stomal opening may be arranged substantially concentric to a stomal opening in the base plate, the opening being accommodated for receiving a stoma. In embodiments, the central section has a substantially circular or oval shape.

In embodiments, the peripheral section is extending radially away from the central section. The peripheral section may circumference the central section or it may extend radially outwards, in one or more directions, from the central section. In embodiments, the peripheral section comprises an elongated shape and extends radially outwards in one direction from the central section. The peripheral section may extend further than the outer rim of the base plate when the sensor patch is applied to such base plate, thereby leaving a part of the peripheral section unattached to the base plate.

In embodiments, the central section comprises a first adhesive and the peripheral section comprises a second adhesive. In embodiments, the first adhesive and the second adhesive are the same adhesive. In embodiments the first adhesive and the second adhesive may have different properties. For example, the adhesives may differ with respect to adhesive tack and/or softness.

The first release liner may be provided with a first tab member for grabbing with the fingers to remove the release liner. Such first tab member may be located at the first release liner near the second edge portion of the sensor patch, the second edge portion being substantially opposite to the first edge portion of the sensor patch.

In embodiments, the first release liner comprises at least two separate or separable parts. A first part of the first release liner may cover a part of the sensor patch overlapping the base plate (when mounted on this) and a second part may cover a part of the sensor patch that is extending further outwards than the base plate. This allows the user to detach the release liner parts one by one, for example remove the first part and apply the thereby exposed side of the sensor patch to the base plate and then subsequently remove the second part of the release liner.

In embodiments, the first release liner is provided with guide means for aligning the sensor patch to the base plate. The guide means may be located on the second part of the first release liner. The guide means may interact with the outer rim of the base plate to ensure correct positioning of the sensor patch on the base plate. In embodiments, the guide means are in the form of a recess or hooks or raised dots adapted to fit against the outer rim of the base plate.

Embodiments relates to a method of attaching a sensor patch to an ostomy base plate comprising the steps of: providing an ostomy base plate with a skin-facing adhesive surface, providing a sensor patch according to claim 1-13, removing the first release liner from the sensor patch and attaching the thereby exposed distal surface of the sensor patch to the adhesive surface of the base plate, removing the second release liner.

Then the base plate can be applied to the skin around a stoma of a patient.

Embodiments, and features of the various exemplary embodiments described in this application, may be combined with each other ("mixed and matched"), unless specifically noted otherwise.

DETAILED DESCRIPTION OF THE DRAWING

Figure 2:
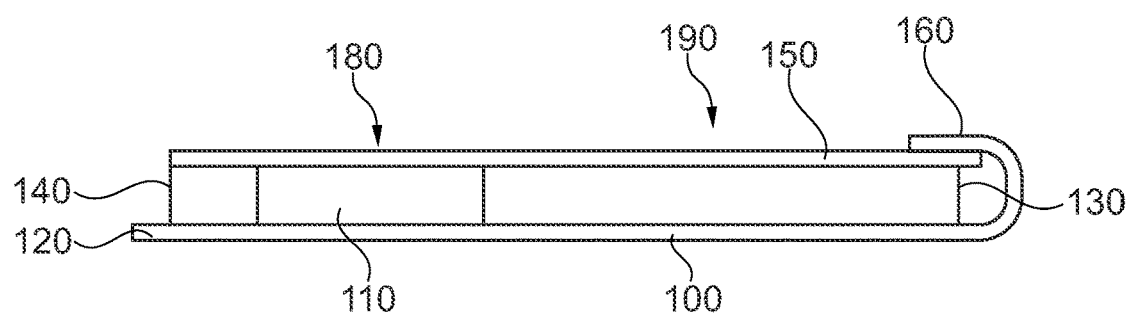
FIG. 2 illustrates the embodiment of FIG. 1 in cross-section.
Figure 3:
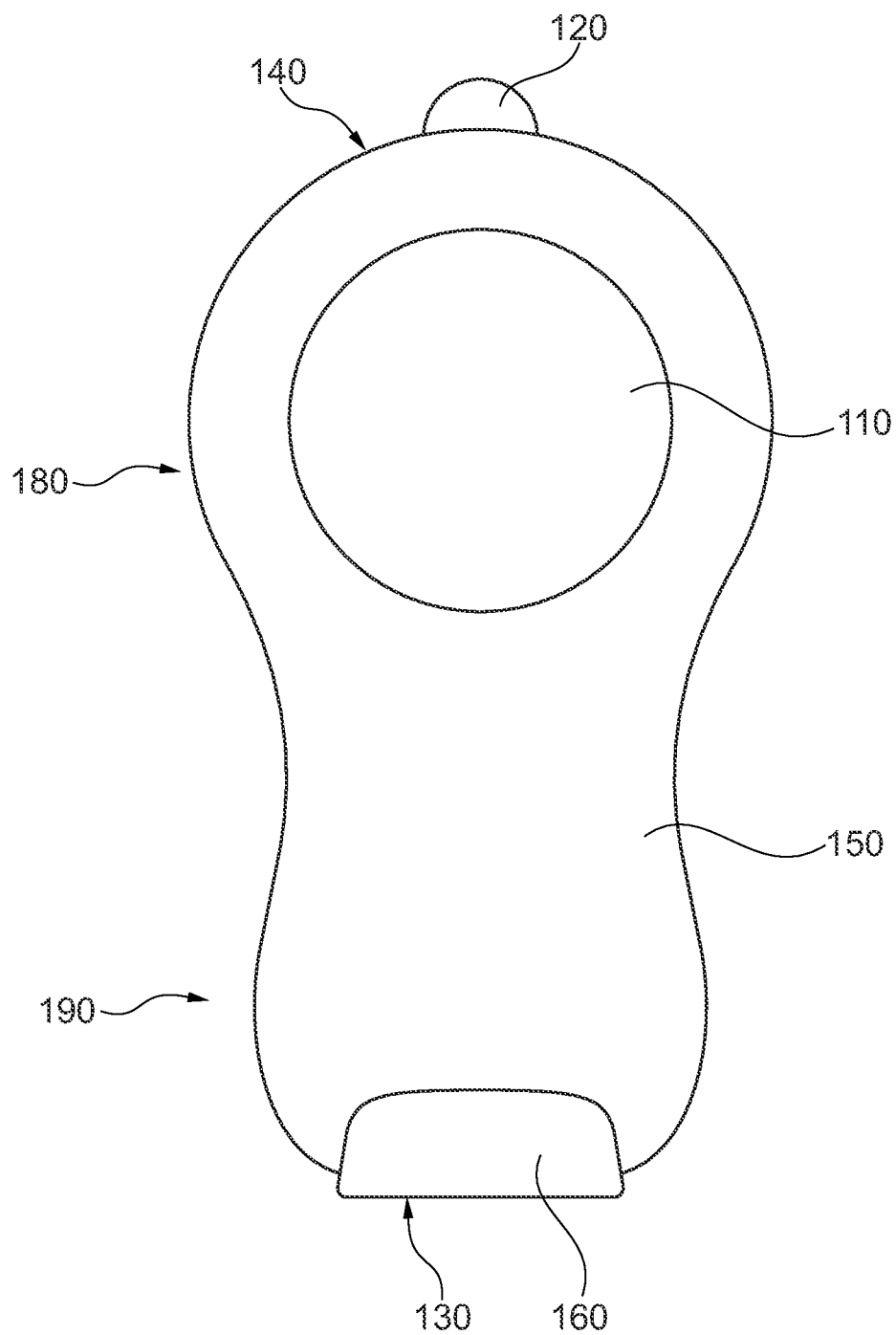
FIG. 3 illustrates the embodiment of FIG. 1 seen from the proximal side.

FIG. 1-3 show an embodiment of a sensor patch, in FIG. 1 seen from the distal side, in FIG. 2 in cross-section and in FIG. 3 seen from the proximal side. The distal side is covered by a first release liner (100) optionally covering the entire distal side. At the second edge portion (140) of the sensor patch is the first release liner extended into a first tab member (120) for use when detaching the first release liner (100) from the distal side of the sensor patch. At the first edge portion (130) of the sensor patch, the first release liner (100) is folded around the first edge portion (130) to overly a part of the proximal side of the sensor patch, at the same time overlying a part of the second release liner (150) and forming an overlapping section (160). The first release liner (100) lies on top of—and adjacent to—the second release liner (150) at the overlapping section (160). The stomal opening (110) is marked in FIG. 1 as a dotted line, indicating that the first release liner (100) covers the opening (110). However, in embodiments, the first release liner (100) is provide with a cut-out corresponding to the stomal opening (110). At the proximal side, shown in FIG. 3, the sensor patch is covered, optionally on the entire proximal side, with a second release liner (150). At the first edge portion (130) a part of the first release liner (100) is folded around the first edge portion (130) to constitute the overlapping section (160). In the shown embodiment, the first edge portion (130) is located at the peripheral section (190) of the sensor patch. At the central section (180) is provided a stomal opening (110) for receiving a stoma.

Figure 4:
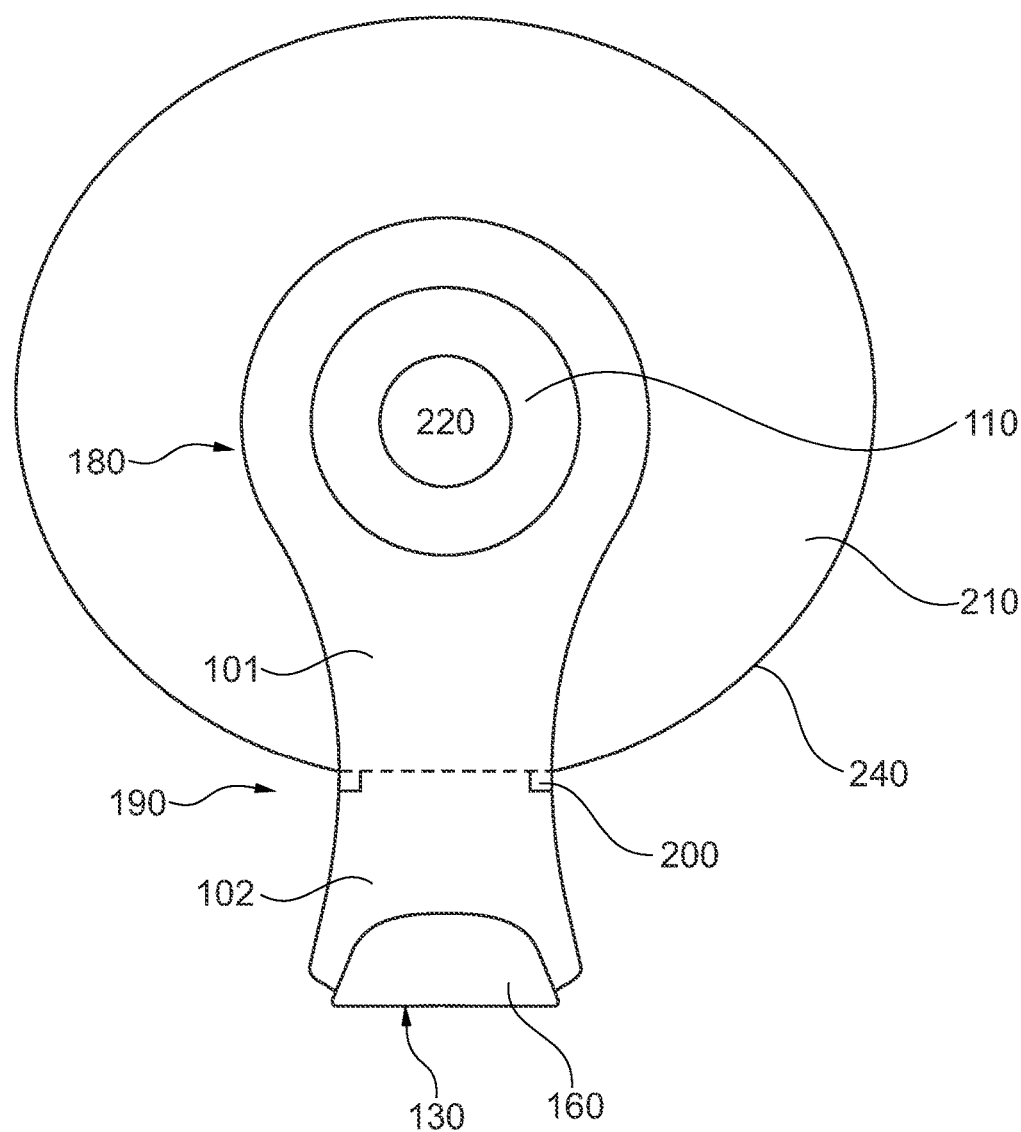
FIG. 4 illustrates an embodiment of a sensor patch attached to a base plate.

In FIG. 4 is shown an embodiment of a sensor patch applied to a base plate (210). The sensor patch is aligned with the base plate (210) in such a way that the stomal opening (110) of the sensor patch is arranged substantially concentric with the stomal opening (220) of the base plate (210). A part of the peripheral section (190) is extending further than the outer rim (240) of the base plate (210). The first release liner is in the form of a first part ((101) and a second part (102), the two parts (101,102) meeting each other's where the peripheral section (190) crosses the outer rim (240) of the base plate (210). At the second part (102) of the first release liner is provided one or more guide means (200). The guide means (200) are configured to fit against the outer rim (240) and thereby secure correct alignment of the sensor patch on the base plate (210). When applying the sensor patch to the base plate (210), the first part (101) of the first release liner is removed while the second part (102) of the first release liner is still present, the guide means (200) are arranged at the outer rim (240) of the base plate (210), thereby securing correct positioning of the sensor patch. When the central section (180) is adhered to the base plate (210), the second part (102) of the first release liner is removed.

Figure 5:
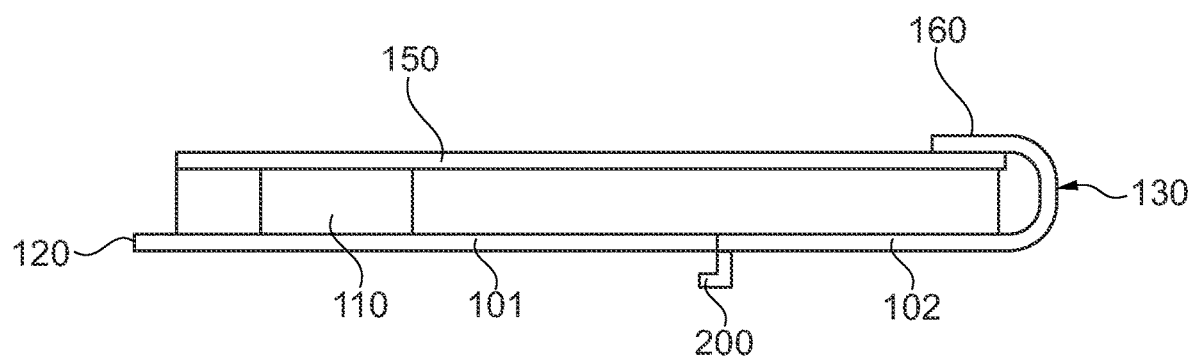
FIG. 5 illustrates an embodiment of a sensor patch in cross-section.

In FIG. 5 is shown an embodiment of the sensor patch with a two-part first release liner (101, 102) and guide means (200). The guide means (200) may for example be in the form of a recess or raised dots or bars.

The invention claimed is:

1. A sensor patch for attachment to a base plate for an ostomy appliance, the sensor patch comprising:
    a distal side and a proximal adhesive side, the distal side being adapted for attachment to a base plate adhesive surface of the base plate, wherein the base plate adhesive surface is adapted for attachment of the base plate to skin of a user;
    a first edge portion and a second edge portion, the second edge portion being positioned longitudinally opposite the first edge portion;
    a first release liner covering the distal side of the sensor patch and a second release liner covering the proximal adhesive side of the sensor patch;
    wherein an overlapping section of the first release liner extends over and around the first edge portion to partially overlap the second release liner and cover a part of a proximal side of the sensor patch;
    wherein the first release liner is inseparably connected to the second release liner at the overlapping section to allow the first release liner to serve as a handle to remove the second release liner.

2. The sensor patch of claim 1, wherein the distal side of the sensor patch is non-adhesive.

3. The sensor patch of claim 1, wherein the first release liner is provided with a liner adhesive adapted for attachment to the distal side of the sensor patch.

4. The sensor patch of claim 1, wherein the second release liner is characterized by an absence of adhesive.

5. The sensor patch of claim 1, wherein the sensor patch comprises a central section and a peripheral section, and the central section of the sensor patch is provided with a stomal opening.

6. The sensor patch of claim 5, wherein the peripheral section of the sensor patch extends radially away from the central section to the first edge portion of the sensor patch.

7. The sensor patch of claim 1, wherein the first release liner is provided with a first tab member that extends beyond the second edge portion of the sensor patch.

8. The sensor patch of claim 1, wherein the first release liner comprises at least two separate and separable portions.

9. The sensor patch of claim 1, wherein the first release liner comprises a first part and a second part, the first part adapted to cover a part of the sensor patch attachable to the base plate and the second part of the first release liner covers a part of the sensor patch adapted to extend longitudinally past a perimeter edge of the base plate.

10. The sensor patch of claim 9, wherein the second part of the first release liner is provided with a guide adapted to align the sensor patch with the base plate.

11. The sensor patch of claim 10, wherein the guide is adapted to align with a perimeter edge of the base plate to ensure correct positioning of the sensor patch on the base plate.

12. The sensor patch of claim 1, the sensor patch further comprising a perimeter defined by an outermost peripheral edge;
    wherein the outermost peripheral edge of the sensor patch, at least at the second edge portion of the sensor patch, is exposed and uncovered by the first release liner and the second release liner.

13. The sensor patch of claim 1, the sensor patch further comprising a perimeter defined by an outermost peripheral edge;
    wherein the second release liner is aligned with and coincident with the outermost peripheral edge of the sensor patch along the second edge portion of the sensor patch.

* * * * *